US009535037B2

(12) United States Patent
Di Lullo et al.

(10) Patent No.: US 9,535,037 B2
(45) Date of Patent: Jan. 3, 2017

(54) APPARATUS AND METHOD FOR MONITORING THE STRUCTURAL INTEGRITY OF A PIPELINE BY MEANS OF A SUPERCONDUCTING MAGNET

(71) Applicant: Eni S.p.A., Rome (IT)

(72) Inventors: Alberto Giulio Di Lullo, Tribiano (IT); Giordano Pinarello, Turin (IT); Alessandro Bailini, Sesto San Giovanni (IT)

(73) Assignee: ENI S.P.A. (IT)

( * ) Notice: Subject to any disclaimer, the term of this patent is extended or adjusted under 35 U.S.C. 154(b) by 137 days.

(21) Appl. No.: 14/364,129

(22) PCT Filed: Dec. 20, 2012

(86) PCT No.: PCT/IB2012/057556
§ 371 (c)(1),
(2) Date: Jun. 10, 2014

(87) PCT Pub. No.: WO2013/098729
PCT Pub. Date: Jul. 4, 2013

(65) Prior Publication Data
US 2014/0312890 A1    Oct. 23, 2014

(30) Foreign Application Priority Data
Dec. 30, 2011  (IT) ............................ MI2011A002451

(51) Int. Cl.
*G01N 27/82*    (2006.01)
(52) U.S. Cl.
CPC ..................................... *G01N 27/82* (2013.01)
(58) Field of Classification Search
CPC ................................ G01N 27/82; G01N 27/72
(Continued)

(56) References Cited

U.S. PATENT DOCUMENTS 4,072,894 A    2/1978  Barton
5,004,724 A *  4/1991  De ..................... G01N 27/9033
                                                       257/32

(Continued)

FOREIGN PATENT DOCUMENTS

DE    1816207 A1    7/1970
EP    0634663 A1    1/1995
JP    60147649 A    8/1985

OTHER PUBLICATIONS

International Search Report dated Mar. 14, 2013 for PCT/IB2012/057556.

*Primary Examiner* — Jermele M Hollington
*Assistant Examiner* — Zannatul Ferdous
(74) *Attorney, Agent, or Firm* — Abel Law Group, LLP

(57) ABSTRACT

An inspection apparatus (100) for monitoring the structural integrity of a pipeline (101) comprising a superconducting electromagnet (102) suitable for generating a magnetic field (106); a cryostat (103) suitable for containing and preserving said superconducting electromagnet (102) at a low temperature; at least two magnetic conveyors (104', 104") connected at opposite ends of the cryostat (103) suitable for conveying the magnetic field (106) generated by the superconducting electromagnet (102) to the wall of the pipeline (101) and facilitating the closing of a magnetic circuit; at least one sensor system (105) for revealing the intensity of the magnetic field (106). A method for monitoring the structural integrity of a pipeline (101) using an inspection apparatus (100) according to the present invention. The inspection apparatus (100) according to the present invention advantageously allows the localization of possible structural imperfections or anomalies of the walls of a pipeline (101), using a more efficient magnet with respect to those normally used in the "pigs" known in the state of the art.

19 Claims, 1 Drawing Sheet

(58) Field of Classification Search
USPC .......................................... 324/240, 242, 220
See application file for complete search history.

(56) References Cited

U.S. PATENT DOCUMENTS

| | | | |
|---|---|---|---|
| 5,134,368 A | 7/1992 | Otaka et al. | |
| 5,845,500 A | 12/1998 | Podney | |
| 5,864,232 A * | 1/1999 | Laursen | G01N 27/902 |
| | | | 324/220 |
| 7,218,102 B2 * | 5/2007 | Nestleroth | G01N 27/82 |
| | | | 324/220 |
| 8,319,494 B2 * | 11/2012 | Simek | G01N 27/87 |
| | | | 324/219 |
| 2007/0195712 A1 * | 8/2007 | Thayer | H04L 67/12 |
| | | | 370/254 |

* cited by examiner

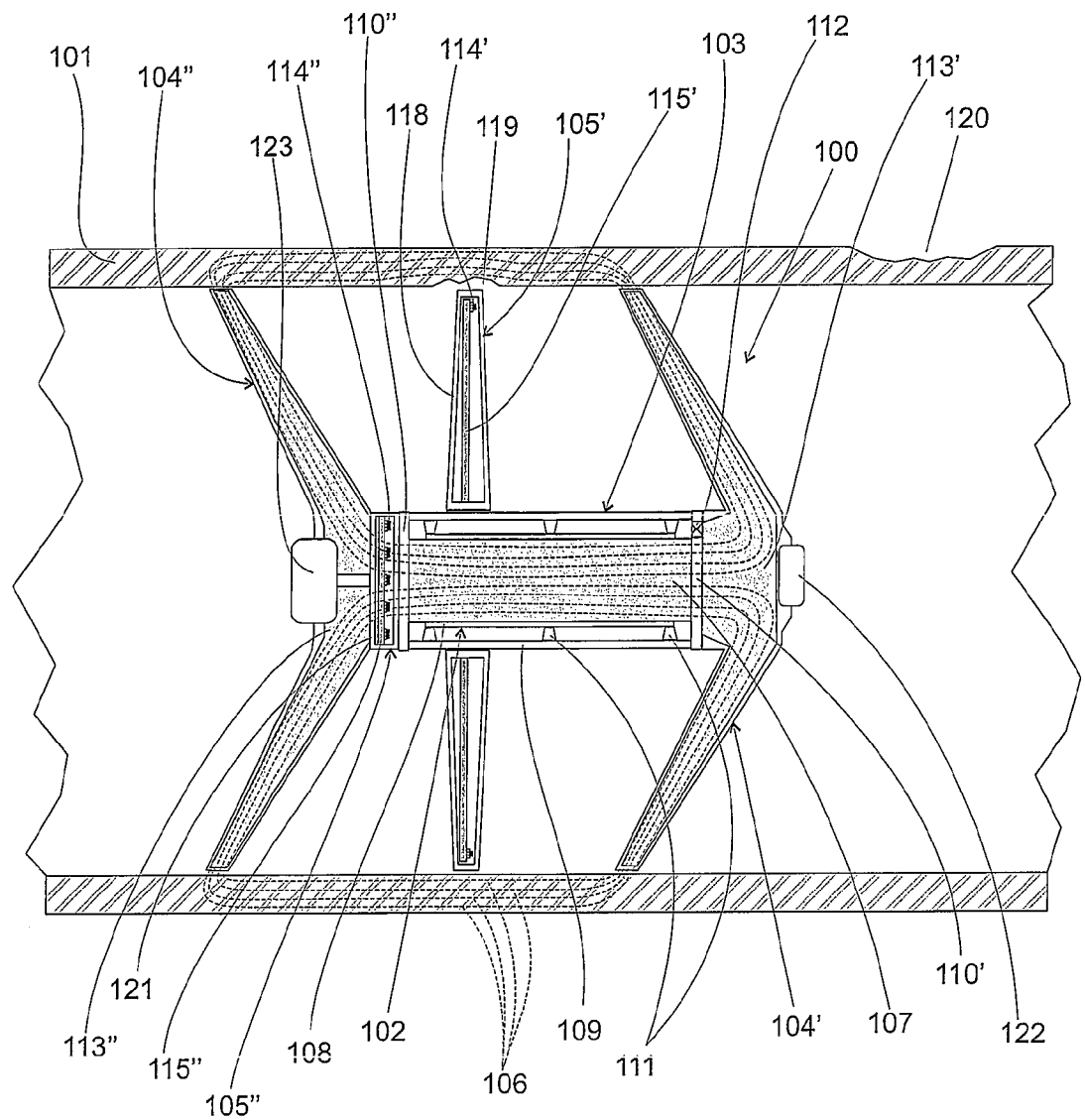

APPARATUS AND METHOD FOR MONITORING THE STRUCTURAL INTEGRITY OF A PIPELINE BY MEANS OF A SUPERCONDUCTING MAGNET

The present invention relates to an inspection apparatus, and the relative method, for determining the structural integrity of a pipeline made of a metallic material.

More specifically, the present invention relates to an inspection apparatus for monitoring the structural integrity of a pipeline, whether it be offshore or onshore, using an inspection device for pipelines, commonly known as "pipeline inspection gauge" or "pig".

There are various methods for inspecting the conditions of a pipeline. These methods normally adopt means known in the art as "pigs" or "foam pigs", the latter being produced in polymeric foam.

Said "pigs" or "foam pigs" are generally in cylindrical form, spherical or bullet-shaped, and are launched or passed into a pipeline for a certain length of the same.

The simplest versions are used for cleaning pipelines, whereas the more evolved versions equipped with electronics and instrumentation onboard, allow various types of measurements and surveys.

An evaluation of the integrity of a pipeline is a fundamental aspect, above all in the oil industry. Possible damage or significant anomalies to the walls of the pipeline can in fact make it unsafe and consequently unusable.

Pipelines carrying gas, petroleum or other oil products can be subject to damage due to various factors, such as, for example, mechanical stress, impact or chemical and electrolytic action of the substances contained therein.

In particular, the thinning of the thickness of a wall of a pipeline in certain points can, with time, lead to ruptures.

Systems for verifying the integrity of a metallic pipeline using magneto-inductive techniques are known in the state of the art.

It is also known that the thinning of the walls of a pipeline causes a variation in the flow of the magnetic field induced in the same. Said magneto-inductive techniques are in fact capable of revealing variations in the thickness of the wall of the pipeline, due for example to thinning or another type of damage.

In these magneto-inductive techniques, a system that is situated inside the pipeline induces a magnetic field in the ferromagnetic wall of the pipeline and contemporaneously effects measurements on the magnetic field induced. In particular, the use of these systems installed in devices for the inspection of pipelines or "pigs" is known in the state of the art.

U.S. Pat. No. 4,072,894, for example, describes an apparatus for non-destructive inspections of pipelines comprising a device capable of generating a magnetic field, spatulas suitable for carrying the magnetic field inside the wall of the pipeline and means for revealing magnetic field losses due to possible thinning or damage to the wall of the pipeline.

The apparatus described in the above patent is extremely bulky and mechanically rigid, and requires a preventive cleaning of the pipeline to be able to operate and avoid operating risks for the same. In fact, in the case of blockage of the apparatus inside the pipeline, due to a narrowing or partial obstruction of the same, the recovery operation of the apparatus requires a considerable operational and consequently economic effort: the more extensive the apparatus, the more difficult it is to recover it from the pipeline in the case of blockage.

Although the apparatus described in the above U.S. Pat. No. 4,072,894 allows possible stress points of the pipeline to be detected, the Applicant has found that it is not without drawbacks and can be improved in various aspects, mainly with respect to the fact that said apparatus requires an accumulator suitable for supplying the electric current necessary for feeding the electromagnet for the whole duration of the monitoring.

Furthermore, in the above patent, the apparatus described is extremely heavy, also due to the battery installed in it, making it extremely difficult for it to advance in the pipeline with the sole thrust caused by the stream flowing therein.

A possible blockage of the apparatus of the pipeline can lead to its temporary disuse. In particular, in the case of a pipeline transporting hydrocarbons, an interruption in the transportation can cause significant economic losses and operational problems for all the phases downstream of the interruption.

In the state of the art, there are also devices or "pigs" equipped with permanent magnets, rather than electromagnets. In this type of apparatus, the magnetic field is generated without the use of electric current.

The Applicant has found however that the permanent magnets used in this type of "pig" are not capable of generating a sufficiently powerful magnetic field in relation to the encumbrance and weight of the magnet used.

The weight and encumbrance of the permanent magnet can in fact complicate the monitoring operation and make it more difficult to recover the "pig" in the case of blockage in the pipeline.

In particular, the Applicant has found that in the case of breakage of the "pig", the permanent magnet contained therein tends to adhere to the walls of the pipeline, due to the magnetic effect, making its recovery more difficult.

An objective of the present invention is to overcome the drawbacks indicated above and in particular to conceive an inspection apparatus for monitoring the integrity of a pipeline, by means of the magneto-inductive technique, which may be more effective with respect to the known technique.

In particular, an objective of the present invention is to provide an inspection apparatus for monitoring the integrity of a pipeline by means of the magneto-inductive technique, which maximizes the magnetic field generated by the magnet in relation to the weight and encumbrance of the inspection apparatus.

A further objective of the present invention is to provide an inspection apparatus for monitoring the integrity of a pipeline, which minimizes the risk of adherence of the magnet to the walls of the pipeline in the case of detachment of the magnet from the inspection apparatus.

Another objective of the present invention is to provide an inspection apparatus for monitoring the integrity of a pipeline which does not require preventive cleaning of the same to be able to be used.

These and other objectives according to the present invention are achieved by providing an inspection apparatus for monitoring the structural integrity of a pipeline by means of a superconducting magnet as specified in claim 1.

Further characteristics of the inspection apparatus for monitoring the structural integrity of a pipeline by means of a, superconducting magnet are object of the dependent claims.

The characteristics and advantages of the inspection apparatus for monitoring the structural integrity of a pipeline by means of a superconducting magnet according to the present invention will appear more evident from the following illustrative and non-limiting description, referring to the enclosed schematic drawing, in which FIG. 1 is a schematic sectional view of a preferred embodiment of an inspection apparatus of a pipeline for monitoring the structural integrity of a pipeline by means of a superconducting magnet.

With reference to FIG. 1, this shows an inspection apparatus of a pipeline, indicated as a whole with 100, for monitoring the structural integrity of a pipeline 101 by means of the magneto-inductive technique.

Said inspection apparatus 100 of a pipeline 101 can comprise:
- a superconducting electromagnet 102 that extends longitudinally in the pipeline 101 suitable for generating a magnetic field 106;
- a cryostat 103 suitable for containing and maintaining said superconducting electromagnet 102 at a low temperature;
- at least two magnetic conveyors 104', 104" connected at opposite ends of the cryostat 103 suitable for conveying the magnetic field 106 generated by the superconducting electromagnet 102 to the wall of the pipeline 101 and facilitating the closing of a magnetic circuit;
- at least one sensor system 105 for revealing the intensity of the magnetic field 106.

According to a preferred embodiment of the present invention, said superconducting electromagnet 102, having a substantially cylindrical form, comprises a nucleus 107 made of a highly magnetic material, preferably consisting of an iron-cobalt alloy, and at least one solenoid 108 which enfolds the nucleus 107, either partially or for its whole length, said solenoid 108 and said nucleus 107 being in contact with each other. For the purposes of the present invention, the term highly magnetic material means a ferromagnetic material having a high magnetic saturation, for example an iron-cobalt alloy.

Said solenoid 108 can be a hollow cylinder made of a superconductor material, preferably a magnesium-diboride or niobium-tin alloy, or a ceramic material.

Said hollow cylinder of the solenoid 108 can have a thickness ranging from 2 to 10 mm.

In an alternative embodiment of the present invention, said solenoid 108 can be a coil, with one or more layers, made of superconductor material, preferably a magnesium-diboride or niobium-tin alloy.

In order to function under superconductor conditions, said superconducting electromagnet 102 must be cooled to cryogenic temperatures, i.e. temperatures lower than 133° K.

In particular, the solenoid 108, if kept at a temperature lower than the critical temperature of the material of which it is made, acts as an electric superconductor opposing a null electric resistance. For example, when the solenoid 108 is made of $MgB_2$, said critical temperature is 39° K.

For the purposes of the present invention, the critical temperature of a material is the temperature below which said material opposes a null electric resistance.

Under these temperature conditions, a possible current induced in the solenoid 108 remains for a long period of time. In particular, the solenoid 108, by opposing a null electric resistance, allows the current induced therein to remain autonomously for as long as there is a superconducting condition, i.e. as long as the temperature of the solenoid 108 is kept below the critical temperature of the material of which it is composed.

As it passes through the solenoid 108, the current induced generates a magnetic field 106 exiting the solenoid 108 axially and penetrating the nucleus 107.

Under cryogenic temperature conditions, the superconducting electromagnet 102 can generate a particularly intense and constant magnetic field. These high performances of the superconducting electromagnet 102 allow, with the same magnetic field generated, a nucleus 107 to be used, having reduced dimensions with respect to traditional magnets or electromagnets used in the "pigs" known in the state of the art, with a consequent reduction in the weight of the inspection apparatus 100.

Alternatively, with the same weight and dimensions of the inspection apparatus 100, the magnetic field 106 is more powerful with respect to traditional magnets or electromagnets used in the "pigs" known in the state of the art.

In order to keep the superconducting electromagnet 102 at cryogenic temperatures for the whole duration of the monitoring operation, said superconducting electromagnet 102 is inserted inside a cryostat 103.

Said cryostat 103 preferably comprises a central body 109, substantially having the shape of a hollow cylinder, and two lids 110', 110", substantially having the shape of a disc, joined to the central body 109 to form a hollow casing.

Said central body 109 is made of a nonmagnetic metallic material, preferably stainless steel, in order to resist mechanical stress and prevent the lines of the magnetic field 106 from closing on the central body 109.

Said lids 110', 110" are made of a ferromagnetic material, preferably an iron-cobalt alloy, in order to guarantee a magnetic permeability to the magnetic field 106 generated by the superconducting electromagnet 102 and limit the gap between said superconducting electromagnet 102 and the magnetic conveyors 104', 104".

Said cryostat 103 also comprises supports 111 made of a material having a low thermal conductivity, preferably Aerogel, suitable for sustaining the superconducting electromagnet 102 and thermally insulating it from the inner surface of the cryostat 103.

In order to limit the heat exchange of the superconducting electromagnet 102 with the cryostat 103, it is also possible to cover the superconducting electromagnet 102 with a layer of superinsulating material (not illustrated) suitable for limiting the radiation.

According to a preferred embodiment of the present invention, in order to keep the superconducting electromagnet 102 at cryogenic temperatures, it is preferable to previously cool it to a temperature lower than that necessary for obtaining the superconductive effect. In particular, it is preferable to cool the solenoid 108 to a temperature lower than half the critical temperature of the material of which it is composed. If the solenoid is made of $MgB_2$, for example, the prior cooling temperature can be 20° K.

Preferably, to cool the superconducting electromagnet 102, it is possible to use an external cooling system (not illustrated).

In particular, said external cooling system can be an immersion cooler of the cryocooler type, i.e. a regenerative heat exchanger used for reaching cryogenic temperatures.

Said external cooling system preferably cools the nucleus 107 when said superconducting electromagnet 102 is already positioned inside the cryostat 103.

In particular, it is possible to put the external cooling system in contact with the nucleus 107, through vacuum thermal contact means (not illustrated) present in the cryostat 103.

Once the desired temperature has been reached for the nucleus 107, the external cooling system is disconnected and the nucleus 107 continues to cool the environment inside the cryostat 103. In particular, the nucleus 107 thus cooled, cools the solenoid 108 bringing it to the temperature necessary for obtaining the electric superconductivity effect.

In order to minimize the heat exchange of the nucleus 107 with the cryostat 103, a vacuum is previously applied inside the cryostat 103.

The absence of air inside the cryostat 103, in fact, allows the heat exchange between superconducting electromagnet 102 and cryostat 103, to be drastically reduced.

The vacuum inside the cryostat 103 is applied by means of a vacuum pump (not illustrated) which is connected to the cryostat 103 by means of a valve 112 present on the cryostat 103.

Alternatively, the superconducting electromagnet 102 can be cooled by inserting a liquid with a low-boiling point, for example liquid helium, inside the cryostat 103.

Said cryostat 103 is capable of maintaining a temperature in its interior, lower than the critical temperature of the material of which the solenoid 108 is composed for a time greater than or equal to 1.2 times the expected duration of the monitoring operation, and in any case for a time not longer than 72 hours, preferably less than 12 hours.

In the case of breakage or fragmentation of the inspection apparatus 100, said cryostat 103 containing the superconducting electromagnet 102 may adhere to the wall of the pipeline due to a magnetic effect.

In spite of this, unlike a permanent magnet, the magnetic effect generated by the superconducting electromagnet 102 tends to weaken with a temperature rise inside the cryostat 103, due to the extinguishing of the superconductivity of the solenoid 108.

Once the nucleus 107 has been cooled, and with this the interior of the cryostat 103, an external solenoid (not illustrated) induces an induced current in the solenoid 108.

By circulating in the solenoid 108 under superconductive conditions, said induced current generates a magnetic field 106 which is stable with time, without the necessity of further electric supply.

Said superconducting electromagnet 102 consequently does not require accumulators inside the inspection apparatus 100, thus significantly reducing the overall weight of the inspection apparatus 100.

Two magnetic conveyors 104', 104" integrally connected to the cryostat 103, in particular to the lids 110', 110" of the cryostat 103, are preferably used for conveying the magnetic field 106 generated by the superconducting electromagnet 102 to the wall of the pipeline 101.

Said magnetic conveyors 104', 104" can be made of a polymeric material and comprise in their interior, a flexible core made of ferromagnetic material 113',113".

In a preferred embodiment, said magnetic conveyors 104', 104" transversally have a disc or daisy shape, and longitudinally an arched shape which takes into account the advance movement of the device, facilitating its passing through the pipeline 101.

Said arched shape also guarantees a constant adhesion of the magnetic conveyors 104', 104" to the internal wall of the pipeline 101, thanks to the elastic thrust that the magnetic conveyors 104', 104" exert on the internal wall of the pipeline 101, once the inspection apparatus 100 has been inserted in the same.

In a particular embodiment of the present invention, the flexible core made of ferromagnetic material 113', 113" of the magnetic conveyors 104', 104" consists of a bundle or pack of steel wires, preferably made of an alloy having a low magnetic saturation, in which the diameter of each wire is less than 0.5 mm and wherein the magnetic permeability of the wire preferably ranges from 1500 to 2000 H/m.

The flexibility of the magnetic conveyors 104', 104" allows the inspection apparatus 100 to overcome any possible section changes of the pipeline 101, due to defects of the same, accumulation areas, deposits, or valves.

In general, said magnetic conveyors 104', 104" optimize the preservation of the magnetic flux and limit the gap between the end of the magnetic conveyors 104', 104" and the internal wall of the pipeline 101.

In a preferred embodiment of the present invention, said system of sensors 105 can be of the LF type 105' (localized fault) or LMA type 105" (loss of metal cross-section area) type.

Said sensor system of the LF type 105' can comprise magnetic sensors 114', suitable for detecting the magnetic field 106, connected to a flexible support 115' made of polymeric material.

Said flexible support 115' of said sensor system of the LF type 105' can have, transversally, a circular or circular-crown form, having an external diameter close to the internal diameter of the pipeline 101, and can be positioned orthogonally with respect to the cryostat 103.

Said magnetic sensors 114' are arranged in a circular configuration substantially along the edge of the flexible support 115', so as to be positioned close to the internal wall of the pipeline 101.

The proximity of said magnetic sensors 114' to the internal wall of the pipeline 101, allows the sensor system of the LF type 105' to reveal local variations in the magnetic field 106, in particular the radial component, close to the wall of the pipeline 101. This type of detection allows useful information to be obtained on the presence and angular position of defects having reduced dimensions 119.

Said sensor system of the LF type 105' can comprise a flexible casing 118 suitable for containing said flexible support 115' and said magnetic sensors 114'. Said flexible casing 118 can be connected to said cryostat 103 orthogonally and extend from this until it touches the internal wall of the pipeline 101.

The flexibility of the flexible casing 118 combined with the flexibility of the flexible support 115' allow the inspection apparatus 100 to pass over any possible deposits or deformations present in the pipeline 101.

Said sensor system of the LMA type 105" can comprise magnetic sensors 114", suitable for detecting the magnetic field 106, connected to a support 115".

Said sensor system of the LMA type 105" can be positioned coaxially with respect to the cryostat 103 and have an essentially circular form.

The coaxial arrangement of the system of sensors of the LMA type 105" allows extensive corrosion phenomena 120 to be revealed, through measuring the total axial magnetic field 106 that passes through the magnetic sensors 114".

Said sensor system of the LMA type 105" can be interposed between one of the magnetic conveyors 104', 104" and said cryostat 103.

Furthermore, said sensor system of the LMA type 105" can comprise a protective shell 121 suitable for protecting and containing the support 115" and magnetic sensors 114" connected to it.

Said inspection apparatus 100 can simultaneously comprise said system of sensors of the LF type 105' and system of sensors of the LMA type 105" or, alternatively, only one of the two.

Said inspection apparatus 100 also comprises a spatial localization system 122 suitable for revealing the positioning of the inspection apparatus 100.

Said spatial localization system 122 comprises a clock (not illustrated) for obtaining a time reference which is associated with at least one position variation measurement, obtained by means of at least one of the following instruments:
- a gyroscope (not illustrated), for determining the inclinations of the inspection apparatus 100;
- an accelerometer (not illustrated) for measuring the acceleration of the inspection apparatus 100 and consequently its variations in velocity;
- a pressure sensor (not illustrated) for revealing the variations in pressure to which the inspection apparatus 100 is subjected, useful for understanding whether the apparatus 100 has passed over possible section changes of the pipeline 101, such as for example welds or valves, having prefixed positions in the pipeline 101.

By associating the data revealed by the sensor system 105 relating to the magnetic field 106, with the data relating to the time reference and position obtained by the localization system 122, it is possible to localize the structural imperfections present on the walls of the pipeline 101.

Said inspection apparatus 100 also comprises electric means 123 suitable for acquiring and storing the data detected by said sensor system 105 and said spatial localization system 122, and suitable for powering said sensor system 105 and said spatial localization system 122.

A further object of the present invention relates to a method for monitoring the structural integrity of a pipeline 101 comprising the phases described hereunder.

As said inspection apparatus 100 does not have its own movement means, it moves in the pipeline 101 thanks to a thrust exerted by the fluid flowing in the same pipeline.

Once inserted in the pipeline 101, the inspection apparatus 100 begins its monitoring operation that lasts until it reaches the receiving trap (not illustrated), wherein the inspection apparatus 100 enters once it has completed its monitoring intervention.

During its monitoring operation, the inspection apparatus 100 generates a magnetic field 106 which is conveyed to the wall of the pipeline 101 by the magnetic conveyors 104', 104" and revealed by the sensor system 105.

In particular, the sensor system 105 reveals variations in the magnetic field 106 that can indicate any possible reduction areas of the thickness of the wall of the pipeline 101.

These data measured by the sensor system 105, together with the data obtained by the spatial localization system 122, are stored by the electric means 123 of the inspection apparatus 100, and can be recovered from the same once the monitoring operation has been completed.

An analysis of the data recovered by the inspection apparatus 100 can provide useful indications with respect to possible structural imperfections 119, 120 present on the walls of the pipeline 101.

Said inspection apparatus for monitoring the structural integrity of a pipeline by means of a superconducting magnet, object of the present invention, is particularly suitable for use in pipelines destined for the transportation of hydrocarbons.

The characteristics of the inspection apparatus and method for monitoring the structural integrity of a pipeline by means of a superconducting magnet, object of the present invention, are evident from the description, as also the relative advantages.

In particular, one of the advantages of the apparatus and method according to the present invention is to allow the localization of possible structural imperfections or anomalies of the walls of a pipeline, by means of a more efficient magnet with respect to those normally used in the "pigs" known in the state of the art.

The superconducting electromagnet of the inspection apparatus according to the present invention is in fact capable of generating a more powerful magnetic field, with the same encumbrance and weight of the inspection apparatus, with respect to that generated by a "pig" equipped with a normal electromagnet or permanent magnet.

Another advantage of the inspection apparatus according to the present invention lies in the fact that, in the case of breakage of the inspection apparatus, the magnetic effect that may tend to cause the superconducting electromagnet to adhere to the wall of the pipeline, tends to become exhausted within a few days, simplifying possible recovery operations of the inspection apparatus or its components.

A further advantage of the inspection apparatus according to the present invention is represented by the fact that the flexible structure of the same allows the inspection apparatus to be utilized for the monitoring of pipelines that have not been previously cleaned of deposits of waxes, paraffins, asphaltenes or sand.

Thanks to its structural flexibility, the inspection apparatus is in fact capable of passing over obstacles and/or partial obstructions present in the pipeline without remaining stuck.

The inspection apparatus is also suitable for being used in pipelines having a small diameter, preferably with a diameter starting from 3 inches.

The apparatus and method for monitoring the structural integrity of a pipeline by means of a superconducting magnet of the present invention thus conceived, can, in any case, undergo several modifications and variants, all included in the same inventive concept. The protection range of the invention is therefore defined by the enclosed claims.

The invention claimed is:

1. A pipeline inspection gauge for monitoring the structural integrity of a pipeline by means of the magneto-inductive technique, characterized in that it comprises
    a superconducting electromagnet suitable for generating a magnetic field comprising a superconductor material,
    a cryostat suitable for containing and maintaining said superconducting electromagnet at cryogenic temperatures which are below a critical temperature of said superconductor material, said critical temperature being a temperature at which said superconductor material opposes a zero electric resistance, and
    at least two magnetic conveyors connected to the cryostat, suitable for conveying the magnetic field generated by the superconducting electromagnet to the wall of the pipeline and facilitating the closing of a magnetic circuit, said magnetic conveyors being made of polymeric material and comprising, in their interior, a flexible core made of ferromagnetic material including a bundle or pack of steel wires.

2. The pipeline inspection gauge according to claim 1, comprising at least one sensor system for revealing the magnetic field.

3. The pipeline inspection gauge according to claim 1, comprising a spatial localization system suitable for revealing the positioning of the inspection gauge.

4. The pipeline inspection gauge according to claim 2, comprising a spatial localization system suitable for revealing the positioning of the inspection gauge, comprising electric means suitable for acquiring and storing the data collected by said sensor system and said spatial localization system, and suitable for feeding said sensor system and said space localization system.

5. The pipeline inspection gauge according to claim 1, wherein said superconducting electromagnet comprises a nucleus in a highly magnetic material and at least one solenoid which enfolds the nucleus and is composed of said superconductor material, said solenoid and said nucleus being in contact with each other.

6. The pipeline inspection gauge according to claim 5, wherein said solenoid is a hollow cylinder made of said superconductor material.

7. The pipeline inspection gauge according to claim 5, wherein said solenoid is a single- or multi-layered coil, made of said superconductor material.

8. The pipeline inspection gauge according to claim 5, wherein a current induced in said solenoid generates a magnetic field axially exiting the solenoid and penetrating the nucleus.

9. The pipeline inspection gauge according to claim 1, wherein said superconducting electromagnet is inserted inside said cryostat in order to maintain the superconducting electromagnet at cryogenic temperatures, for the whole duration of the monitoring operation.

10. The pipeline inspection gauge according to claim 9, wherein said cryostat comprises a central body and two lids joined to the central body to form a hollow casing.

11. The pipeline inspection gauge according to claim 1, wherein said superconducting electromagnet comprises a nucleus in a highly magnetic material and at least one solenoid which enfolds the nucleus and is composed of said superconductor material, said solenoid and said nucleus being in contact with each other, wherein said cryostat comprises thermal contact means under vacuum, through which an external cooling system comes into contact with the nucleus in order to cool it.

12. The pipeline inspection gauge according to claim 11, wherein the vacuum is created inside said cryostat in order to minimize the heat exchange of the nucleus with the cryostat.

13. The pipeline inspection gauge according to claim 2, wherein said sensor system-is of the LF type or LMA type.

14. The pipeline inspection gauge according to claim 13, wherein said sensor system of the LF type suitable for revealing local variations in the magnetic field close to the wall of the pipeline, comprises magnetic sensors, connected to a flexible support and arranged in a circular configuration substantially along the edge of the flexible support.

15. The pipeline inspection gauge according to claim 13, wherein said sensor system of the LMA type, suitable for measuring the total axial magnetic field, positioned coaxially with respect to the cryostat, comprises magnetic sensors connected to a support.

16. The pipeline inspection gauge according to claim 3, wherein said spatial localization system comprises a clock for obtaining a time reference which is associated with at least a measurement of the variation in the position, obtained by means of at least one of the following instruments:
    a gyroscope;
    an accelerometer;
    a pressure sensor.

17. A method for monitoring the structural integrity of a pipeline which comprises the following steps:
    providing a pipeline inspection gauge according to claim 1;
    inserting said pipeline inspection gauge into the pipeline for a monitoring operation;
    generating a magnetic field by means of said pipeline inspection gauge, which is conveyed to the wall of the pipeline;
    revealing, by means of said pipeline inspection gauge, the variations in the magnetic field conveyed to the wall of the pipeline;
    storing said data relating to the variations in the magnetic field in the pipeline inspection gauge;
    recovering said data relating to the variations in the magnetic field from the pipeline inspection gauge;
    analyzing said data relating to the variations in the magnetic field to obtain indications with respect to possible structural imperfections present on the walls of the pipeline.

18. The pipeline inspection gauge according to claim 1, which is adapted for monitoring the structural integrity of a pipeline destined for transporting hydrocarbons.

19. The pipeline inspection gauge according to claim 1 wherein said superconducting electromagnet generates the magnetic field while not connected to an external power source, said superconducting electromagnet including a nucleus of a highly magnetic material and at least one solenoid which enfolds the nucleus, said solenoid being made of said superconductor material.

* * * * *